United States Patent [19]

Dindi et al.

[11] Patent Number: 5,527,936
[45] Date of Patent: Jun. 18, 1996

[54] HYDROSILYLATION OF UNSATURATED COMPOUNDS

[75] Inventors: Hasan Dindi, Ponca City, Okla.; Basil Gregorovich, Wilmington, Del.; Isidor Hazan, Clementon, N.J.; Stuart Milligan, Ponca City, Okla.

[73] Assignee: E. I. du Pont de Nemours and Company, Wilmington, Del.

[21] Appl. No.: 390,340

[22] Filed: Feb. 17, 1995

[51] Int. Cl.$^6$ ................................ C07F 7/08; C07F 7/18
[52] U.S. Cl. ............................... 556/479; 556/470
[58] Field of Search ...................... 556/479, 470

[56] References Cited

U.S. PATENT DOCUMENTS

| | | | |
|---|---|---|---|
| 2,524,529 | 10/1950 | Krieble | 260/448.2 |
| 2,533,240 | 12/1950 | Goldblatt et al. | 260/448.2 |
| 2,570,463 | 10/1951 | Lipscomb | 260/448.2 |
| 4,161,572 | 7/1979 | Yonezawa et al. | 525/100 |
| 4,188,454 | 2/1980 | Foley et al. | 428/391 |
| 4,579,966 | 4/1986 | De Pasquale et al. | 556/482 |
| 5,281,636 | 1/1994 | Nambu et al. | 524/378 |

FOREIGN PATENT DOCUMENTS

WO94/06807  3/1994  WIPO.

*Primary Examiner*—Paul F. Shaver
*Attorney, Agent, or Firm*—James A. Costello

[57] ABSTRACT

A method for hydrosilylating an olefinically unsaturated compound comprising contacting the unsaturated compound with a source of silicon in the presence of an azo-containing free-radical catalyst, the hydrosilylated product being a useful crosslinking agent.

15 Claims, No Drawings

HYDROSILYLATION OF UNSATURATED COMPOUNDS

BACKGROUND OF THE INVENTION

1. Field of the Invention

This invention pertains to a process for making silicon-containing compounds employing an azo free-radical initiation system.

2. Description of Related Art

There are generally three methods for adding a silane to an olefinic compound. They are the Grignard method, the precious metal catalyst route and the free-radical route. The method employed in the process of this invention is characterized by the following advantages: (1) reaction products have excellent crosslinking properties as a result of their enrichment in disilylated component; (2) reactions proceed safely, quickly, and with good yield; (3) the initiators are highly selective for the desired products; (4) no separation of initiator is necessary since formation of byproducts is minimal and the products do not harm the system; (5) substantially no undesirable color is introduced into the final products by initiator or byproduct; and (6) economical compared to the precious metal catalyst route.

Despite the known methods for adding an olefinic compound to a silane, none has employed an azo free-radical initiator with the particular olefinic substrates described in the process of this invention characterized as it is by having at least 10 percent of a disilylated component in the final hydrosilylated product. Careful selection of the olefinic compound, choice of azo free-radical initiation, and production of at least 10 percent of disilylated material in the final product achieves process advantages 1 to 6 described above. These products have special utility in a wide range of compositions that cure in the presence of atmospheric moisture; for example, sealants, caulks and the like.

SUMMARY OF THE INVENTION

This invention pertains to a method for hydrosilylating (i) an olefinically unsaturated compound comprising contacting the unsaturated compound with (ii) a source of silicon in the presence of (iii) an azo initiator; wherein (i) is selected from at least one member of the group:

myrcene,
ocimene,
alloocimene,
limonene,
menthadiene,
phellandrene,
terpinene,
terpinolene,
isoterpinolene,
carvone
citronellal,
citral,
cyclooctadiene,
4-vinyl-1-cyclohexene, and
norbornadiene;

wherein at least 10 percent by weight of the hydrosilylated product is disilylated.

The preferred olefinically unsaturated compounds are selected from limonene (dipentene, ψ-limonene, R-(+)-limonene and its stereoisomers); 4-vinyl-1-cyclohexene; and norbornadiene. Preferred products comprise at least 30% of disilylated component, more preferably 50%, most preferably above 75%. Most especially preferred is substantially completely (>90%) disilylated product. To obtain products that are especially useful in certain applications, it may be preferred to operate the process of this invention on olefinic compounds containing internal unsaturation, including internal diunsaturation.

The source of silicon (ii) has the formula

wherein:

R is independently selected from alkyl, alkoxy, aryl, aryloxy, cycloalkyl, hydrocarbyl, acyloxy, and oxysilyl;

X is independently selected from halogen;

j is independently 1 to 3;

l and k are independently 0 to 3; and j+k+l=4.

R moieties can be substituted, as will be appreciated by one skilled in the art, provided the substituents do not interfere with the reactants, the reaction mechanism or the reaction products. Preferably, j=1.

Useful azo initiators have the following general formula:

wherein:

$R_1$ and $R_2$ are the same or different and are selected from the group cyanoalkyl, cyanocycloalkyl, alkoxycyanoalkyl, heterocyclo alkyl, alkyl alkoxy esters, aryl alkoxy esters, alkyl aroyl esters, aryl aroyl esters, substituted and unsubstituted alkyl amides, cyanocarboxylic acids, and carbamoyl.

Representative of the preferred azo initiators that can be employed in the process of this invention are 2,2'-azobis(2-methylbutanenitrile), 1,1'-azobis(cyclohexanecarbonitrile), and 2,2'-azobisisobutyronitrile. The elementary stage of free radical formation is shown below for the class of azo initiators contemplated in the process of this invention:

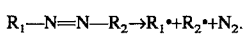

DETAILS OF THE INVENTION

Compounds are made having an average number of silane groups of at least 1.1 by reacting one mole of an olefinically unsaturated compound with sufficient silane (to obtain the desired degree of disilylation) in the presence of a free-radical initiator. The resulting product is then reacted with an alcohol (preferably a $C_1$–$C_{18}$ alcohol) or alcohol derivative such as sodium methoxide and the like (if the silane was, say, halo-substituted) to displace the halogens and give a compound having one or more trialkoxysilyl groups. $C_1$ to $C_4$ alcohols are most preferred, especially methanol and ethanol.

Alternatively, the unsaturated compound can be reacted with a trialkoxysilane to give the desired compound directly. Other silanes having a Si—H bond can also be used. The resulting silane-functional compounds are useful as crosslinking agents in polymer compositions. The following reaction sequence is a representative route (unbalanced) to a durable, film-forming disilylated reaction product:

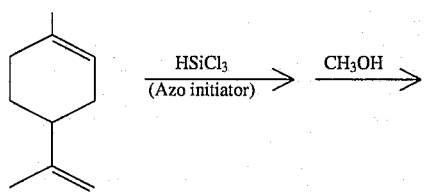

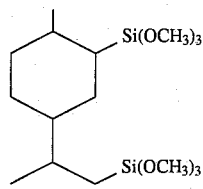

R-(+)-limonene
(or stereoisomers)

Representative silicon sources (ii) include trichlorosilane, triethoxysilane, dichlorosilane, dichloromethylsilane, dichloroethylsilane, dichloromethoxysilane, dichloroethoxysilane, chlorodimethoxysilane, chlorodiethoxysilane, and the like. Representative azo initiators are listed in Table 1:

TABLE 1

2,2'-azobis(2,4-dimethylpentane nitrile)
2,2'-azobis( 2-methylbutanenitrile)
1,1'-azobis(cyclohexanecarbonitrile)
2,2'-azobis(N,N'-dimethyleneisobutyramidine)dihydrochloride
2,2'-azobis(2-amidinopropane)dihydrochloride
2,2'-azobis(N,N'-dimethyleneisobutyramidine)
4,4'-azobis(4-cyanopentanoic acid)
2,2'-azobis(2-methyl-N-(1,1-bis(hydroxymethyl)-2-hydroxyethyl)propionamide)
2,2'-azobis(2-methyl-N-(1,1-bis(hydroxymethyl)ethyl)propionamide)
2,2'-azobis(2-methyl-N-(2-hydroxyethyl)propionamide)
2,2'-azobis(isobutyramide)dihydrate
2,2'-azobis(4-methoxy-2,4-dimethylvaleronitrile)
2,2'-azobisisobutyronitrile
dimethyl 2,2'-azobisisobutyrate
2-(carbamoylazo)isobutyronitrile
2,2'-azobis( 2,4,4-dimethylpentane)
2-phenylazo-2,4-dimethyl-4-methoxyvaleronitrile, and
2,2'-azobis(2-methylpropane).

Contemplated ethylenically unsaturated compounds are listed in Table 2, and include isomers and tautomers thereof as well as such compounds substituted with substituents that do not interfere with the hydrosilylation reaction disclosed herein.

TABLE 2

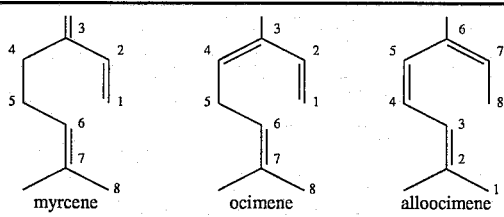

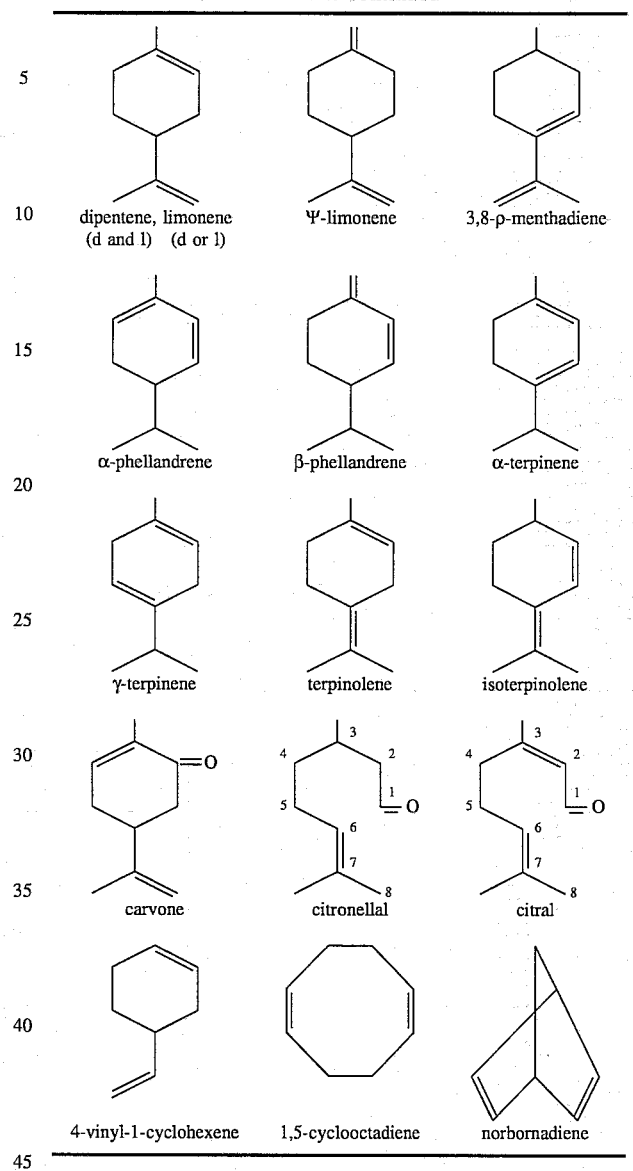

The process of this invention can be run in batch, semi-continuously or in a continuous stirred reactor with initiator added as needed. The following Examples are representative in which product quantities are in weight percent. The disilylated components in these Examples are approximately as follows:

| Example No. | Disilylated Product (%) |
| --- | --- |
| 1 | 50 |
| 2 | 75 |
| 3 | 80 |
| 4 | 90 |
| 5 | 80 |
| 6 | 75 |
| 7 | 75 |
| 8 | 85 |
| 9 | 40 |
| 10 | 30 |
| 11 | 10 |
| 12 | 30 |

EXAMPLE 1

The reactor was a 300 ml cylindrical pressure reactor made of Hastelloy® and equipped with a double-paddle agitator, a thermocouple, a pressure gauge, heating mantle, injection port (dip tube) and a discharge port on the head space opening to the atmosphere through a dry-ice trap.

To this reactor was added 17 g of R-(+)-limonene (0.125 mole), 68 g of trichlorosilane (0.5 mole, 100% excess) and 1 g of 2,2'-azobis(isobutyronitrile) (VAZO® 64; 2% of stoichiometric reactants), and the reactor was sealed. The mixture in the reactor was heated with stirring to 80° C. and kept at 80° C. for 4 hours. The reactor was then cooled to ambient temperature and the remaining trichlorosilane (TCS) was removed by nitrogen purge and vacuum. A Gas Chromatography analysis showed that the product mixture contained 5% limonene, 40% of mono-substituted product: 1-methyl-4-(trichlorosilyl-2-propyl) cyclohex-1-ene and isomers thereof, 50% of disubstituted product: 1-methyl-4-(trichlorosilyl-2-propyl)-2-trichlorosilylcyclohexane and isomers thereof; and 5% other. VAZO is a registered trademark of E. I. du Pont de Nemours and Company.

EXAMPLE 2

To the reactor described in Example 1 was added 34 g of R-(+)-limonene, 136 g of TCS and 2 g of VAZO® 64. The reaction mix was held at 90° C. for 4 hours. After removing the unreacted TCS, the GC analysis showed that the product mixture contained 0.3% of R-(+)-limonene, 20% of mono-substituted product: 1-methyl-4-(trichlorosilyl-2-propyl)cyclohex-1-ene and isomers thereof, 75% of di-substituted product: 1-methyl-4-(trichlorosilyl-2-propyl)-2-trichlorosilylcyclohexane and isomers thereof, and 5% of others.

EXAMPLE 3

To the reactor described in Example 1 was added the same ingredients as in Example 2. The reaction temperature was held for 5 hours. GC analysis showed 0.3% of R-(+)-limonene, 15% of mono-substituted product: 1-methyl-4-(trichlorosilyl-2-propyl)cyclohex-1-ene and isomers thereof, 80% of di-substituted product: 1-methyl-4-(trichlorosilyl-2-propyl)-2-trichlorosilylcyclohexane and isomers thereof, and 5% others.

EXAMPLE 4

The reaction products of Examples 1, 2 and 3 were combined to obtain a 250 gram mixture. GC analysis showed the mixture was made of 1% R-(+)-limonene, 20% of mono-substituted product: 1-methyl-4-(trichlorosilyl-2-propyl)cyclohex-1-ene and isomers thereof, 74% of di-substituted product: 1-methyl-4-(trichlorosilyl-2-propyl)-2-trichlorosilylcyclohexane and isomers thereof, and 5% others. This mix was placed in a 600 ml Hastelloy® pressure reactor which, except for volume, is otherwise identical to the 300 ml reactor employed in Example 1. To this reactor was added 67 g (about 0.5 mole) of TCS and 1 g of VAZO® 64. The reactor was sealed and the mixture was brought to 90° C. and kept at this temperature for 2 hours. A GC analysis showed that the mixture contained 0.5% of R-(+)-limonene, 6% of monosubstituted product, 90% of di-substituted product and 3.5% of others.

EXAMPLE 5

To the reactor described in Example 4 was added R-(+)-limonene (136 g, 1 mole), trichlorosilane (406 g, 3 mole, 50% excess), and 2,2'-azobis (2-methylbutanenitrile) (VAZO® 67, 8 g, 2% of stoichiometric reactants). The mixture was slowly heated to 85° C. with stirring and was held at 85° C. for 3 hours. GC analysis showed 18% of mono-substituted product: 1-methyl-4-(trichlorosilyl-2-propyl)cyclohex-1-ene and isomers thereof; and 80% of disubstituted product: 1-methyl-4-(trichlorosilyl-2-propyl)-2-trichlorosilylcyclohexane and isomers thereof. Conversion of limonene to hydrosilylated products was higher than 98%.

EXAMPLE 6

A 2-neck, 500 mL round-bottom flask was equipped with a magnetic stirring bar, heating mantle, solids addition funnel, and condenser. The condenser was fitted with a Claisen adapter and a polytetrafluoroethylene-clad thermocouple was inserted through the Claisen adapter and condenser to reach the liquid layer of the flask. The other arm of the Claisen adapter was connected to a 250 mL liquid addition funnel fitted with a Dewar condenser. The entire assembly was purged with nitrogen prior to the reaction and a positive pressure of nitrogen was maintained during the reaction.

The roundbottom flask was charged with R-(+)-limonene (136 g, 1 mole). The solids addition funnel was charged with 10 g of VAZO® 64. The liquid addition funnel was charged with trichlorosilane (271 g, 2 mole). The condenser on the flask and the condenser on the solids addition funnel were cooled to −10° C. Stirring was started and the flask contents were heated. Once the flask temperature exceeded 90° C., enough trichlorosilane was added to bring the flask temperature to about 85° C. Small quantities of VAZO® 64 were added intermittently. The temperature was maintained between 85°–90° C. by adding trichlorosilane and small amounts of initiator as needed.

Excess trichlorosilane in the reaction mixture was evaporated by passing nitrogen over the reaction mixture and recondensing trichlorosilane in the liquid addition funnel. At this point, the temperature was allowed to rise to 125° C., then held for 1 hour. The total reaction time was 15 hours. The reaction mixture was then cooled to ambient temperature and the product isolated by standard inert atmosphere techniques. A GC analysis showed that the reaction mixture contained 2% of R-(+)-limonene, 20% of mono-substituted product: 1-methyl-4-(trichlorosilyl-2-propyl) cyclohex-1-ene and isomers thereof, and 75% of di-substituted product: 1-methyl-4-(trichlorosilyl-2-propyl)-2trichlorosilylcyclohexane and isomers thereof, with 3% others.

EXAMPLE 7

A 4-liter glass resin kettle with a glass lid containing four standard-taper ground glass joints was equipped as described in Example 6 except for the use of a 2-liter, jacketed resin kettle replacing the trichlorosilane addition funnel. Reaction was carried out as in Example 6 using R-(+)-limonene (1362 g, 10 mole), trichlorosilane (2844 g, 21 mole) and VAZO® 64 (80 g). After 24 hours of reaction, GC analysis showed that the reaction product consisted of 19% of mono-substituted hydrosilylation product: 1-methyl-4-(trichlorosilyl-2-propyl)cyclohex-1-ene and isomers thereof; 78% of di-substituted hydrosilylation product: 1-methyl-4-(trichlorosilyl-2-propyl)-2-trichlorosilylcyclohexane and isomers thereof, 0.2% of R-(+)-limonene, and 3% of others.

EXAMPLE 8

To the reactor described in Example 7 was added R-(+)-limonene (1362 g, 10 mole), trichlorosilane (2710 g, 20 mole) and 2,2'-azobisisobutryonitrile polymerization initiator (80 g, 2% of stoichiometric reactants). The procedure described in Example 7 was used. After 30 hours of reaction, the GC analysis showed 10% of mono-substituted product: 1-methyl-4-(trichlorosilyl-2-propyl) cyclohex-1-ene and isomers thereof; and 85% of disubstituted product: 1-methyl-4-(trichlorosilyl-2-propyl)-2-trichlorosilylcyclohexane and its isomers. This hydrosilylation product was then methoxylated using methanol and analyzed using KIDS (Potassium Ionization of Desorbed Species), and was determined to be higher than 98% disubstituted methoxylated silane product: 1-methyl-2-trimethoxysilyl-4-(trimethoxysilyl-2-propyl) cyclohexane and its isomers.

EXAMPLE 9

A 2-neck, 100 mL round-bottom flask was equipped as described in Example 6 except for the use of a 50 mL liquid addition funnel. Reaction was carried out as in Example 6 using norbornadiene (18.4 g, 0.2 mole), trichlorosilane (60.4 g, 0.45 mole) and VAZO® 64 (3 g). After isolation, GC analysis using an internal standard indicated that some of the norbornadiene was consumed giving both mono-substituted product: 5-(trichlorosilyl)bicyclo[2.2.1]hept-2-ene and isomers thereof and di-substituted product: 2,5-bis(trichlorosilyl)bicyclo[2.2.1]heptane and isomers thereof.

EXAMPLE 10

A 2-neck, 100 mL round-bottom flask was equipped as described in Example 6 except for the use of a 50 mL liquid addition funnel. Reaction was carried out as in Example 6 using 4-vinyl-1-cyclohexene (22 g, 0.2 mole), trichlorosilane (57 g, 0.4 mole) and VAZO® 64 (3 g). After isolation, GC analysis using an internal standard indicated that the vinylcyclohexene was consumed giving both monosubstituted product: 4-(2-trichlorosilylethyl)cyclohex-1-ene and isomers thereof and disubstituted product: 4-(2-(trichlorosilylethyl)-1-trichlorosilylcyclohexane and isomers thereof.

EXAMPLE 11

A 2-neck, 100 mL round-bottom flask was equipped as described in Example 6 except for the use of a 50 mL liquid addition funnel. Reaction was carried out as in Example 6 using 1,5-cyclooctadiene (0.3 mole, 33 g, 37 mL), trichlorosilane (0.315 mole, 43 g, 32 mL) and VAZO® 88 (1.5 g). After isolation, GC analysis indicated that about 20% of monosubstituted products (5-trichlorosilylcyclooctene and its isomers) and about 10% of disubstituted products (1,5-di(trichlorosilyl)-cyclooctane) were formed.

EXAMPLE 12

To the reactor described in Example 7 was added dipentene (1230 g, 9 mole), trichlorosilane (2500 g, 18 mole) and 2,2'-azobisisobutyronitrile (115 g) and 1,1'-azobis(cyclohexanecarbonitrile) (20 g) polymerization initiators. The procedure described in Example 7 was used. After 38 hours of reaction, the GC analysis showed 10% mono-substituted products: 1-methyl-4-(2-propyl(1-trichlorosilyl))-1-cyclohexene, 1-methyl-2-trichlorosilyl-4-(2propenyl)cyclohexane and their isomers; and 30% of di-substituted products: 1-methyl-2-trichlorosilyl-4-2-propyl(1-trichlorosilyl))cyclohexane and its isomers.

We claim:
1. A method for hydrosilylating (i) an olefinically unsaturated compound comprising contacting the unsaturated compound with (ii) a source of silicon in the presence of (iii) an azo initiator; wherein (i) is selected from at least one member of the group, including their isomers:

myrcene,
ocimene,
alloocimene,
dipentene
limonene,
menthadiene,
phellandrene,
terpinene,
terpinolene,
isoterpinolene,
carvone,
citronellal,
citral,
4-vinyl-1-cyclohexene, and
norbornadiene;
(ii) is selected from the group $H_jSiR_kX_l$ wherein:
R is independently selected from alkyl, alkoxy, aryl, aryloxy, cycloalkyl, hydrocarbyl, acyloxy, and oxysilyl;
X is independently selected from halogen;
j is independently 1 to 3;
l and k are independently 0 to 3; and
j+k+l=4.
wherein at least 10 percent by weight of the hydrosilylated product is disilylated.

2. A method according to claim 1 wherein (i) is selected from limonene, 4-vinyl-1-cyclohexene and norbornadiene.

3. A method according to claim 2 wherein (i) is limonene.

4. A method according to claim 3 wherein (ii) is trichlorosilane.

5. A method according to claim 1 wherein (iii) is selected from at least one member of the group:
2,2'-azobis(2,4-dimethylpentane nitrile)
2,2'-azobis(2-methylbutanenitrile)
1,1'-azobis(cyclohexanecarbonitrile)
2,2'-azobis(N,N'-dimethyleneisobutyramidine)dihydrochloride
2,2'-azobis(2-amidinopropane)dihydrochloride
2,2'-azobis(N,N'-dimethyleneisobutyramidine)
4,4'-azobis(4-cyanopentanoic acid)
2,2'-azobis(2-methyl-N-(1,1-bis(hydroxymethyl)-2-hydroxyethyl)propionamide)
2,2'-azobis(2-methyl-N-(1,1-bis(hydroxymethyl)ethyl)propionamide)
2,2'-azobis(2-methyl-N-(2-hydroxyethyl)propionamide)
2,2'-azobis(isobutyramide)dihydrate
2,2'-azobis(4-methoxy-2,4-dimethylvaleronitrile)
2,2'-azobisisobutyronitrile
dimethyl 2,2'-azobisisobutyrate
2-(carbamoylazo)isobutyronitrile
2,2'-azobis(2,4,4-dimethylpentane)
2-phenylazo-2,4-dimethyl-4-methoxyvaleronitrile, and
2,2'-azobis(2-methylpropane).

6. A method according to claim 2 wherein (ii) is trichlorosilane and (iii) is azobis(2-methylbutanenitrile).

7. A method according to claim 2 wherein (ii) is trichlorosilane and (iii) is azobis(isobutyronitrile).

8. A method according to claim 1 comprising the additional step of reacting the hydrosilylated reaction product with an alcohol.

9. A method according to claim 2 comprising the additional step of reacting the hydrosilylated reaction product with an alcohol.

10. A method according to claim 3 comprising the additional step of reacting the hydrosilylated reaction product with an alcohol.

11. A method according to claim 4 comprising the additional step of reacting the hydrosilylated reaction product with an alcohol.

12. A method according to claim 5 comprising the additional step of reacting the hydrosilylated reaction product with an alcohol.

13. A method according to claim 8 wherein the alcohol is a $C_1$ to $C_{18}$ alcohol.

14. A method according to claim 9 wherein the alcohol is a $C_1$ to $C_{18}$ alcohol.

15. A method according to claim 10 wherein the alcohol is a $C_1$ to $C_{18}$ alcohol.

* * * * *